United States Patent [19]

Marsden

[11] Patent Number: 4,816,683
[45] Date of Patent: Mar. 28, 1989

[54] CATHODE/CONVERTER

[76] Inventor: Paul K. Marsden, 26 Cotswold Road, Sutton, Surrey, England

[21] Appl. No.: 23,198

[22] Filed: Mar. 9, 1987

[30] Foreign Application Priority Data

Mar. 12, 1986 [GB] United Kingdom ............... 8606086

[51] Int. Cl.$^4$ ............................................. G01T 1/185
[52] U.S. Cl. ................................. 250/385.1; 250/374
[58] Field of Search ............... 250/385.1, 374; 219/68, 219/69 R, 69 M

[56] References Cited

U.S. PATENT DOCUMENTS

| 3,971,942 | 7/1976 | Seidman et al. | 250/369 |
| 4,320,299 | 3/1982 | Bateman et al. | 250/385.1 |
| 4,485,307 | 11/1984 | Osborne et al. | 250/385.1 |
| 4,725,705 | 2/1988 | Holland-Moritz et al. | 219/69 M |
| 4,735,678 | 4/1988 | Mandigo et al. | 219/69 M |

FOREIGN PATENT DOCUMENTS

| 1389028 | 4/1975 | United Kingdom . |
| 1525712 | 9/1978 | United Kingdom . |
| 1556441 | 11/1979 | United Kingdom . |
| 1571666 | 7/1980 | United Kingdom . |
| 1601406 | 10/1981 | United Kingdom . |

OTHER PUBLICATIONS

Lim et al., "Characteristics of Multiwire Proportional Chambers for Positron Imaging", IEEE Trans. Nucl. Sci., 21, 1974, pp. 85–88.
Chu et al., "High Efficiency Collimator-Converters for Neutral Particle Imaging", IEEE Trans. Nucl. Sci., 23 (1), pp. 634–639, Feb. 1976.

Primary Examiner—Carolyn E. Fields
Attorney, Agent, or Firm—Harness, Dickey & Pierce

[57] ABSTRACT

A combined cathode/converter for the ionization chamber of a MWPC photon detector comprising an array of rectangular wells in a layer of lead or lead alloy, formed by spark-erosion machining. The thickness of the walls and floor of each well is so as to maximize the efficiency of the detector by increasing the surface area to volume ratio of the cathode/converter.

5 Claims, 3 Drawing Sheets

CATHODE/CONVERTER

The invention relates generally to combined cathode/converters for use in gas filled radiation detectors such as those used to detect high energy photons, for instance X-ray or gamma rays, and particularly but not exclusively for use in a "positron camera" used in Nuclear Medicine for forming 3D X ray images of patients.

Most imaging in Nuclear Medicine is carried out using radiopharmaceuticals labelled with $^{99}Tc^m$, imaged in vivo with a gamma camera. Images, taken up to 3h after injection, may be planar static, dynamic or tomographic in nature. As most imaging agents are not disease specific, contrast between abnormal and normal function is often poor. Tomography, in the form of Single Photon Emission Computed Tomography (SPECT) can improve this contrast. This is usually performed by rotating a gamma camera around the patient, taking multiview images, and producing sectional images of the body using computer reconstruction techniques. However, the sensitivity of a gamma camera is only 0.1% with a typical collimator, and produces images with a spatial resolution of about 2cm at the centre of a patient.

An alternative imaging method which should be capable of greater spatial resolution and sensitivity is Positron Emission Tomography (PET). This is carried out using radionucleides which emit positrons. The resultant interactions of these positrons in tissue takes place of the order of 1 mm from the point of emission and produce two photons which are emitted at 180° apart. These are then detected in coincidence by two detectors placed on opposite side of the object. PET detectors do not require collimators and, hence, have the intrinsically good spatial resolution and sensitivity required. However, the available detectors are far too expensive and inflexible for routine Nuclear Medicine use, and there is therefore a need for a low cost, yet highly efficient, photon detector.

Such a detector could be based, for instance, on Multiwire Proportional Chamber (MWPC) technology in which a photon impinging on a high density converter causes emission of a fast electron which can be detected in a conventional proportional chamber consisting of one or more anodes and cathodes and a chamber gas such as an argon/methane mixture.

Most detectors of this type constructed to date have followed one of two design strategies. The first uses a single MWPC plane placed behind a high density converter incorporating drift channels which is typically 1 cm thick. The converter consists of either a laminar structure including layers of lead with drift holes drilled into it, or a matrix of lead-glass tubes. 511 kev photons are converted to fast electrons in the lead, and these electrons escaping from the lead into the hole/tube cause ionisation in a chamber gas. The resulting electron shower is drifted down the tube by an applied field and detected by the MWPC. This type of system has a high intrinsic spatial resolution of at best 2 mm, and a time resolution of at best 2 = 40 nS (in neon). An alternative approach, is to construct a stack of MWPC anode planes interleaved with lead foil plates which serve both as cathode and converter. This has the advantage of a high timing resolution of 2~10nS (in isobutane) and a spatial resolution of ~5 mm.

The main drawback of all MWPC based systems is their relatively low sensitivity, resulting in long imaging times and low signal to noise ratios when compared with other systems such as multicrystal ring systems.

It has been found that a remarkable increase in efficiency of the detector can be obtained by using a cathode/converter which is in the form of an array of open cells. The construction of such an array from substances which are typically used for cathode/converters, for instance lead or lead alloy, is made difficult because such substances are often relatively soft and so cannot easily be machined to the small dimensions necessary.

It has also been discovered that spark-erosion machining (also known as electrodischarge machining or EDM) —a technique previously used on hard metals—is surprisingly successful at producing the required pattern of cells for the cathode/converter.

Accordingly, the present invention provides a structure adapted to function in use as a combined cathode/converter for a gas filled radiation detector, characterised in that the structure includes an array of cells formed in the converter material by electro-discharge machining (EDM). The cells may conveniently be formed by spark-erosion machining a layer of suitable cathode/converter material, preferably lead or lead alloyed with antimony, bismuth or copper.

The present invention thus further provides method of making a cathode/converter comprising a layer of lead or other soft, suitable material, in which surface machining of the layer, such as to produce the array of cells is carried out by spark erosion.

The array of cells is preferably a regular array of rectangular pits extending all the way through the converter material with the wall thickness being in the range 40 to 80 $\mu m$. The pitch of the pattern and the well depth are both preferably in the range 0.5 to 1.5 mm. The "honeycombed" lead may be supported by a laminar substrate consisting of a lower layer of a grp (glass reinforced plastics) board, and an upper layer of copper, similar to the type of board used for pcbs (printed circuit boards) in electronics. The cathode/converter according to the invention would be used in a manner entirely analogous to that of conventional cathode/converters i.e. interleaved in a stack of anodes e.g. made from wire mesh surrounded by a chamber gas such as an argon/methane mixture. The detection of the ionising electrons occurs in the same way as in conventional MWPC's and the supporting hardware and software to process and analyse the events may be conventional.

According to a further aspect the invention provides a structure according to the first aspect of the invention and wherein the cells are open at each of their ends.

According to yet a further aspect the present invention provides a neutral particle detector comprising means defining a chamber, the chamber being filled with an ionising chamber gas and, disposed inside the chamber, at least one stack of combined cathode/converters and with meshed anodes interleaved with said converters, the combined cathode/converters being structures including an array of cells defined in the converter material, the cells being formed in the converter material by electro-discharge machining.

The invention may also be used in a positron detector where one or more pairs of detectors are used, the members of each pair being arranged opposite one another.

The invention will be further described by way of non-limitative example with reference to the accompanying drawings, in which.

Figure 1:
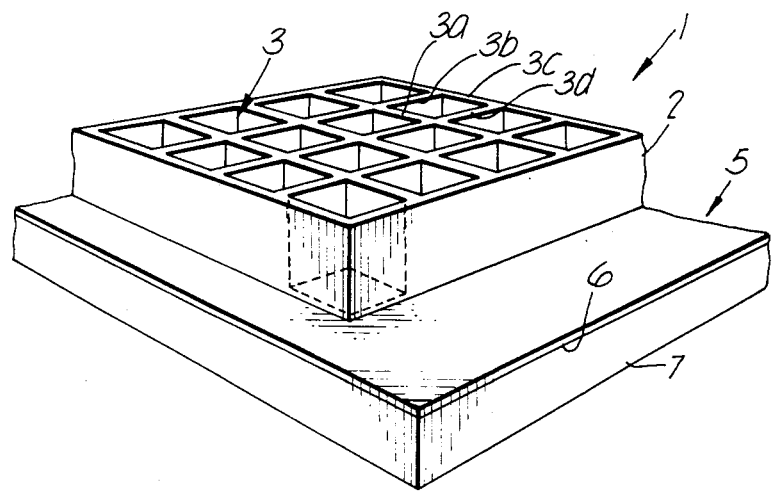
FIG. 1 is a close-up view of part of a cathode/converter according to an embodiment of the invention.

FIG. 1 shows a section of the operative part of a cathode/converter (1) according to the present invention to be in the form of an array of rectangular, open cells (3), formed by spark erosion in a thin layer of lead alloy (2). Each cell (3) is square in cross section and defined by four walls (3a–3d) and extends completely through the layer of lead alloy (2). The layer of lead alloy is supported by a laminar substrate (5) comprising an upper layer of copper (6) and a lower layer of grp board (7). The thickness of each cell wall is about 40–80 $\mu$m and the pitch and depth of the alloy in the range 0.5 to 1.55 mm. It will be appreciated that the whole cathode/converter will comprise hundreds, sometimes thousands, of the cells as shown in FIG. 1.

Figure 2:
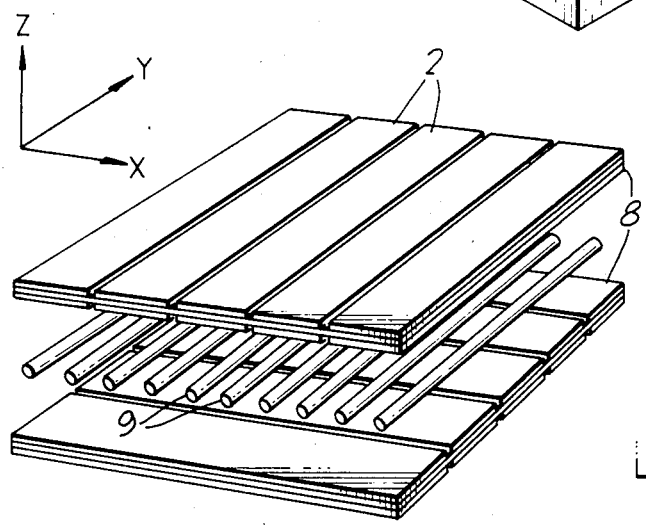
FIG. 2 is a schematic diagram of a stack of MWPC's and cathodes/converters according to the present invention.

A number of the cathode/converters (1) are incorporated in a photon detector as shown in FIG. 2. The detector comprises, in a stacked arrangement parallel overlying cathode/converters (8) interleaved with a similar number of anode planes (9). Each cathode/converter consists of two layers of lead, each 125 um thick, which are laminated onto opposite sides of a thin plastic foil. In this embodiment, the plastic foil is 75 um thick. Each layer of lead has the "box" pattern (not shown in FIG. 2) reproduced on its surface as shown in FIG. 1. The lead layers are also divided into strips, as shown, by narrow interstrip gaps. As explained below, this allows the coordinates of a detected event to be ascertained. The width of the gap is less than 1 mm. The strips in the cathode/converter planes (8) are aligned either in the direction marked X or Y (perpendicular to the plane of the paper) as shown in FIG. 2. The anode consists of 20 um gold plated tungsten wires. The anode cathode gap is about 2.5 mm and the pitch of the wires in the anode plane, 1–2 mm. The anode planes are parallel to the cathode/converter planes as shown. The anodes and cathodes, with suitable bias potentials applied to them form the electrodes of the proportional chamber.

The orthogonal orientation of the cathode strips in successive planes allows the X and y coordinates of an incident detected photon to be ascertained to within a few millimeters. The incident photon produces a fast electron in one of the cathode/converter planes. The fast electron escapes and is detected in the proportional chamber by virtue of the shower of secondary electrons it produces in the gas in the chamber. The electron shower is detected at the anode and a pulse is induced in the two adjacent cathode planes. Thus, the alternating orientation of the strips in each successive cathode plane allow the X and Y coordinates of the event to be ascertained. The Z coordinate is fixed by the corresponding pulse in the anode. The subsequent processing of the signals from the detector is done by conventional electronics.

Turning now to the manufacture of the cathode/converter of lead or lead alloy, in spark-erosion machining, an anode with the mirror image of the required pattern is cut out of graphite, copper or tungsten and this may then be used to erode the pattern into a plane lead sheet. The anode is raised to high electrical potential relative to the plane lead sheet and is then lowered towards the lead sheet until electrical discharges occur between the two. The space between the anode and lead is filled with a dielectric fluid which flushes away the waste metal from the lead sheet. This process is continued until the required pattern has been cut. A lead-antimony or lead-calcium alloy may be used to provide a harder base material for the erosion. The electrical discharge between anode and workpiece liberates heat; given, therefore the relatively low melting point of lead one would not expect the process to be capable of producing an accurate pattern of the small size required. It is found, however, that the quality of product from EDM is sufficient to give the desired increase in detector sensitivity.

Figure 3:
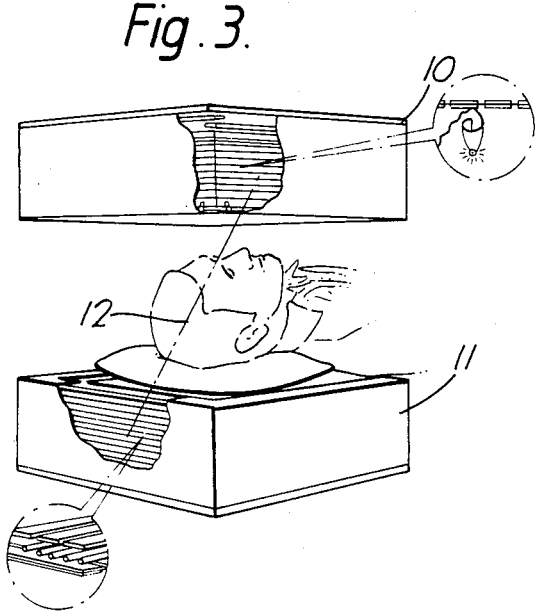
FIG. 3 illustrates schematically the imaging technique and arrangement using a positron camera.

A complete system for imaging internal organs is shown schematically in FIG. 3. Two detectors are used (10) and (11)—one on each side of the patient. The isotope (12) in the patient's organs emit positrons, which anhiliate within a few millimeters to produce photons travelling at 180° to each other. The detectors (10) and (11) detect the photons as described, and conventional digital electronics equipment is used to detect the coincidences and isolate "good" events. Rotation of the detectors around the patient then allows fully 3D images to be produced.

Figure 4:
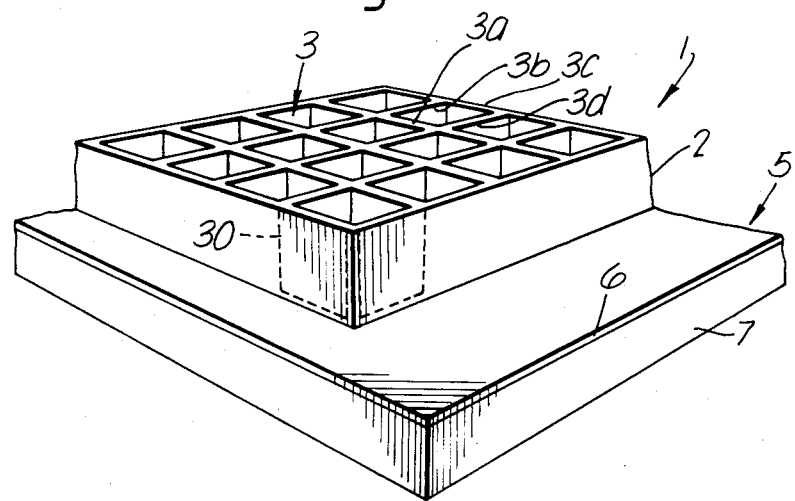
FIG. 4 shows an alternative embodiment of the present invention.

In the embodiment described above the cells in the converter material extend all the way through it. However, as an alternative the cells do not extend completely through the layer but instead have a floor 30 as shown in FIG. 4. The cathode/converter of FIG. 4 is made by Electro-discharge machining and is used in detectors in exactly the same way as that of FIG. 1. The performance of the cathode/converter of FIG. 4 has been found not to be quite as good as that of FIG. 1 and this is believed to be due to the decrease in probability of escape of an electron formed in the converter more than cancelling out the effect of the increase in surface area of converter material.

The design of the detector may be optimized by the following analysis. The efficiency of an individual photocathode is a product of three parameters.

(i) The probability of an incident photon producing a fast electron in the lead by either a photoelectric or Compton interaction—at 511 keV the cross section is approximately the same for each interaction.

(ii) Due to multiple scattering the primary electron distribution can be considered to be isotropic with a well defined range. The probability of the electron escaping into the chamber gas and causing ionisation therefore depends on the photocathode structure—in particular its surface area to volume ratio.

In a stacked detector the optimum foil properties are a compromise between (i) and (ii). If attenuation in the foil is too great, then photons are lost that could have been detected on the succeeding foils of the stack, if it is less, more converters will be needed in the stack to obtain the same total efficiency. It is seen that the optimum photocathode depends on the number of photocathodes employed, and it is easily shown that the total detector efficiency is proportional to the electron escape factor of one photocathode. Increasing the escape factor for one photocathode will thus increase the detector efficiency by the same amount provided the charge collection is not degraded.

(iii) Secondary electrons produced in the gas are collected to produce a detectable signal at one of the anodes—if the collecting field is too low electrons may diffuse back onto the lead surface and be lost. (Also the fast electron path length must not be limited to such an extent that it does not cause sufficient ionisation). This effect is obviously more important for a photocathode structure such as in FIG. 1 than for a plain one. In this case the field must remove electrons from the "well" before there has been significant lateral diffusion.

Figure 5:
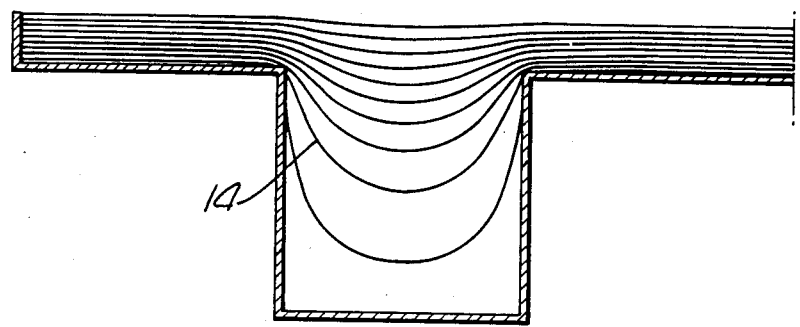
FIG. 5 is a diagram showing the electric field within each lead cell of a cathode/converter according to the present invention.

FIG. 5 shows the result of a 3D calculation of the equipotentials (14) inside a cubic well (i.e similar to that in the cathode/converter of FIG. 1 but with a floor) with the approximation that the equipotentials run parallel to the converter plane as they would for a flat cathode, two well depths away from it. It is found that for a cubic well as shown the field at the very bottom of the well is about 5% of the field in the uniform regions outside the well (i.e. beyond the influence of the well), which is assumed to be roughly the same as that for a plane cathode. The field at the surface of a plane cathode with the 2.5 mm anode to cathode gap of the present embodiment is calculated to be ~8 kV/cm giving the lowest field within the well as ~400 V/cm. The average value is much higher. This field is sufficiently high to remove electrons from the well. Note also that the field is everywhere directed away from the walls of the well which thus opposes the effects of diffusion of the secondary electrons.

Figure 6:
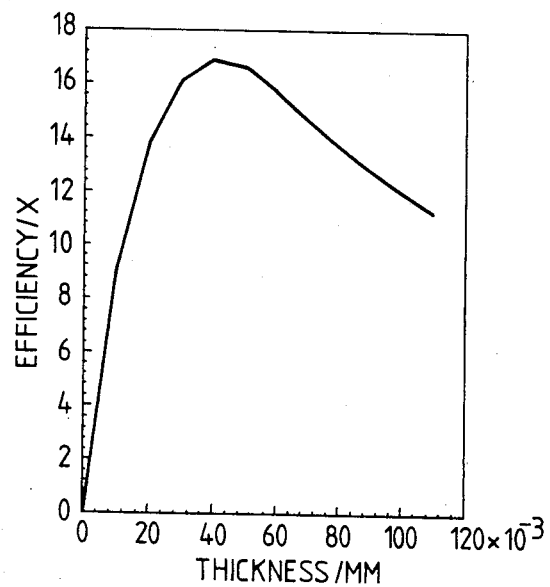
FIG. 6 is a graph of efficiency as a function of cell-wall thickness for a 20 layer MWPC embodying the present invention.

FIG. 6 shows the efficiency v converter foil thickness for a detector with 20 box pattern converter planes (as in FIG. 1 with 1 mm pitch of the box pattern) at 511 keV—it is seen that the optimum foil thickness lies between 40 and 50 mm, giving an efficiency of about 17%.

Figure 7:
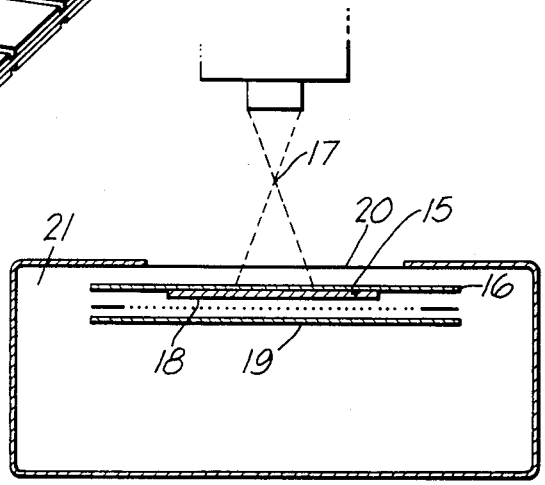
FIG. 7 illustrates an arrangement used to test the efficiency of the cathode/converter.

The efficiency of a detector may be measured with the arrangement of FIG. 7 with measurements being performed on a single converter for which photon attenuation is small. Since photoelectrons from 511 keV photons have a practical range of 50 $\mu$m in lead only a surface layer of ~50 $\mu$m can contribute to electron detection and the efficiency is expected to be proportional to the surface area of the foil if secondary electron collection is complete, i.e. if the collecting electric field is high enough and the fast electron path length is not limited to such an extent that it does not cause sufficient ionization. It is only when multiple converters are considered and attenuation effects become important that the measurement becomes sensitive to foil thickness.

The efficiencies of three single 10 cm×10 cm converter foils were measured. The first consisted of a plane lead sheet 250 $\mu$m thick. The second was a 0.5 mm thick lead sheet into which 750 $\mu$m wide and 350 $\mu$m deep slots were milled on a 1 mm pitch and the third was a box pattern converter as in FIG. 4 with 150 $\mu$m wide, 650 $\mu$m deep walls on a 750 $\mu$m pitch. Note that for all the converters the walls are much thicker than the 50 $\mu$m the maximum electron range mentioned above. The converters (15) were mounted on a 1.6 mm grp printed circuit board type base (16). The conversion efficiency for 511 keV positron annihilation photons from a 22 Na source (17) was measured in a simple MWPC with one wire plane (18) and two plane cathodes—one of these being the converter (16) and the other a grp board with a copper surface (19). The wire plane (18) consisted of 20 $\mu$m wires on a 2 mm pitch and the anode to cathode gap was 4 mm, i.e. larger than the 2.5 mm gap on the full size prototype. A MELINEX window (20) on the front of the detector allows the background due to interactions of photons with the chamber gas to be measured and subtracted. The gas (21) used was an 80/20 mixture of argon/methane which provided stable operation with an EHT of 3 kV. The MWPC was operated in coincidence with a NaI scintillator resulting in a well defined "projection area" on the converter.

The following efficiencies were measured:

| converter | relative surface area | measured efficiency |
|---|---|---|
| plane | 1.0 | 0.94 +/− 0.1 E-3 |
| slotted | 1.8 | 2.06 +/− 0.1 E-3 |
| box pattern | 4.8 | 3.8 +/− 0.15 E-3 |

The results above indicate that the converter efficiency does increase in proportion to its surface area and a factor of 5 increase in the efficiency of a single converter is likely to be obtainable for a converter with a wall thickness of between 40 and 50 $\mu$m. A detector comprising of 20 such converter planes will have an efficiency 3.5 times that of the prototype detectors with similar scatter detection properties, and a complete system operating in coincidence will have a sensitivity 10 times that of the prototype.

A complete 2 or 4 detector PET system could use 60 cm×30 cm converters and would be capable of producing fully 3-dimensional, high resolution images of large volumes, in imaging times of several minutes.

I claim:

1. A neutral particle detector comprising means defining a chamber, the chamber being filled with an ionising chamber gas and, disposed inside the chamber, at least one stack of combined cathode/converters and wire anodes interleaved with said converters, the combined cathode/converters being structures including an array of cells defined in the converter material, the cells being formed in the converter material by electro-discharge machining.

2. A positron detector apparatus for detecting coincidences of photons emitted from a sample, comprising at least one pair of detectors, each detector of the pair comprising means defining a chamber, the chamber being filled with an ionising chamber gas and, disposed inside the chamber, at least one stack of combined cathode/converters and with anodes interleaved with said converters, the combined cathode/converters being structures including an array of cells defined in the converter material, the cells being formed in the converter material by electro-discharge machining.

3. A method of forming a cathode/converter for use in an ionization chamber which comprises the step of electro-discharge machining a surface of the converter material to define therein an array of open cells.

4. A method according to claim 3 wherein the converter material is lead or lead alloy, the array of cells is a regular array of cuboidal wells in the converter material the thickness of the walls between each cell being in the range 25 to 125 $\mu$m and the pitch and depth of the cells being in the range 0.5 to 1.5 mm.

5. A method according to claim 3 wherein the machining is continued through the depth of the material to form cells which are open to each of two opposed surfaces of the material.

* * * * *